United States Patent [19]

Steffen

[11] 4,268,698
[45] May 19, 1981

[54] METHOD OF PREPARING BIS-(CHLOROMETHYL)-TETRACHLOROBENZENES

[75] Inventor: Klaus D. Steffen, Hennef-Geisbach, Fed. Rep. of Germany

[73] Assignee: Dynamit Nobel Aktiengesellschaft, Cologne, Fed. Rep. of Germany

[21] Appl. No.: 82,385

[22] Filed: Oct. 5, 1979

Related U.S. Application Data

[63] Continuation of Ser. No. 3,553, Jan. 15, 1979, abandoned, which is a continuation of Ser. No. 895,186, Apr. 10, 1978, abandoned, which is a continuation of Ser. No. 748,266, Dec. 7, 1976, abandoned.

[30] Foreign Application Priority Data

Dec. 13, 1975 [DE] Fed. Rep. of Germany ....... 2556322

[51] Int. Cl.³ ............................................. C07C 25/14
[52] U.S. Cl. .................................................. 570/198
[58] Field of Search ................................... 260/651 R

[56] References Cited

U.S. PATENT DOCUMENTS 2,817,632 12/1957 Mayor ............................. 260/651 R
2,979,448 4/1961 Miller ............................. 260/651 R Primary Examiner—O. R. Vertiz
Assistant Examiner—Wayne A. Langel
Attorney, Agent, or Firm—Sprung, Felfe, Horn, Lynch & Kramer

[57] ABSTRACT

Process of preparing bis-chloromethyl tetrachlorobenzene of the formula

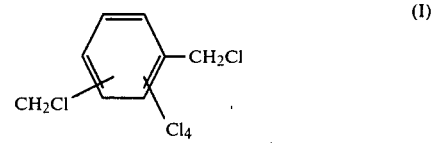

In a first stage xylene is contacted with chlorine for formation of tetrachloroxylene, in the presence of iron chloride catalyst. In a second stage the tetrachloroxylene is contacted with chlorine for formation of (I), in the presence of radical catalyst. According to the invention, the second stage is performed in the presence of iron chloride catalyst from the first stage and in the presence of hexamethylenetetramine for complexing with the iron chloride catalyst. Thereby the iron chloride catalyst does not interfere with the second stage.

13 Claims, No Drawings

METHOD OF PREPARING BIS-(CHLOROMETHYL)-TETRACHLOROBENZENES

This is a continuation of application Ser. No. 003,553, filed Jan. 15, 1979, abandoned, which is a continuation of application Ser. No. 895,186, filed Apr. 10, 1978, abandoned, which is a continuation of application Ser. No. 748,266, filed Dec. 7, 1976, abandoned.

BACKGROUND

The subject matter of the present invention is a method of preparing o-, m- and p-bis-(chloromethyl)-tetrachlorobenzenes of the general formula

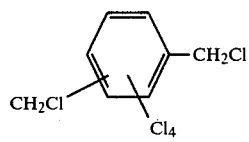

characterized in that o-, m- or p-xylene is chlorinated radically on the side-chains in the presence of hexamethylenetetramine (HMTA) in a one-pot process, after completion of an iron chloride-catalyzed nuclear chlorination.

In Houben-Weyl 5/3, p. 740, there is described a method of preparing 1,4-bis-(chloromethyl)-2,3,5,6-tetrachlorobenzene from p-xylene; here the method is practiced in nickel autoclaves using liquid chlorine at 12 to 15 atmospheres gauge pressure. For the technical preparation of this compound, nickel autoclaves are quite expensive, and chlorine under this pressure always constitutes a source of danger.

The chloromethylation of tetrachlorobenzene with bis-(chloromethyl) ether in the presence of fuming sulfuric acid is suitable only on a laboratory scale (Z. L. Vejdelek and M. Protiva, Collection Czechoslov. Chem. Commun. 39 (1974) 6, 1596). Also poorly suitable for industrial purposes is the preparation of the three isomeric bis-(chloromethyl)-tetrachlorobenzenes from the dioxonium compounds of tetra-(nucleus)-chloroxylenes with carbon tetrachloride and water (German "Offenlegungsschrift" No. 2,211,735).

The chlorination of xylene with chlorine gas in a one-pot process, i.e., the chlorination of the nucleus as well as the side chains in the same reaction vessel, is particularly suitable for the economical, technical preparation of bis-(chloromethyl)-tetrachlorobenzenes as in German Pats. 1,568,607 and 2,358,949. In the process of the first of these two patents, the nuclear chlorination is performed in a first step with a small amount of ferric chloride catalyst (0.05 to 1.0 wt.-% with respect to xylene), so as not to excessively impair the side-chain chlorination in the second step, the overall result being poor utilization of the chlorine, with poor yields and low purity.

In a criticl departure from this method, German Pat. No. 2,358,949 proposes the use of ultraviolet light to activate chlorine gas in the gas phase over the reaction solution, and then to agitate the surface of the reaction solution intensely to enable it to absorb the activated chlorine gas.

However, this method also has its disadvantages: A large surface is achieved only by intense agitation and a relatively wide reaction vessel; high-powered stirrers consume energy, and nowadays space-saving, slender reaction vessels of great useful capacity are preferred in the art. Furthermore, the emerging hydrogen chloride gas always carries with it a more or less great amount of chlorine gas, and it is desirable that the chlorination take not too long a time. In this process, however, the excitation of the chlorine gas in the second step by means of radical initiators is difficult or impossible. It has been found that the presence of iron chloride catalysts greatly impairs or destroys the effectiveness of the radical catalysts added in the second step.

THE INVENTION

The subject of the invention is a method of preparing o-, m- or p-bis-(chloromethyl)-tetrachlorobenzenes, characterized in that, setting out from o-, m- or p-xylene, the nuclear chlorination is performed in the first step in the presence of iron chloride catalysts, and then the chlorination of the side chains is performed radically in the presence of hexamethylenetetramine.

The reaction is performed at atmospheric pressure or at a slight superatmospheric pressure of the chlorine.

The term, "iron chloride catalysts," as used herein, is to be understood to refer especially to $FeCl_3$, or also $FeCl_3.6H_2O$.

The amounts of the iron chloride catalysts are to be from about 0.5 to 5%, and preferably 1.0 to 2.5%, by weight, with respect to the xylenes.

Chlorinated, low-boiling aliphatic hydrocarbons having boiling points from 60° to about 80° C. can serve as solvents, carbon tetrachloride being greatly preferred.

It is very advantageous that the solvent and the starting substances do not have to be dried to an extreme degree. Moisture contents such as form due to exposure to moist air will do no harm, but heavy contamination with water must be eliminated by drying.

Hexamethylenetetramine (HMTA) is known to be a complexing agent for many metal salts, for example, of the elements Co, Ni, Fe, Cu, Cd, Mn, Ca, Hg, Pt, and Cr, examples of such complex salts being $HMTA.2CuCl_2$ or $Co(NO_3)_2.2HMTA.9H_2O$ (L. Vanino and A. Schinner, Arch. Pharm. 252 (1914) 449; A. Premel-Cabic and J.-E. Guerchais, C.R. Acad. Sci. Ser. C. 272 (1971) 1133). Vanino states that the $FeCl_2$ and $FeCl_3$ complex compounds decompose at room temperature, while the other metal complexes are easily isolatable and stable.

All of these metal complexes are easily soluble in water.

It was therefore quite surprising that HMTA forms with ferric chloride complex compounds which are stable even at temperatures of 75° C., that this complex compound is stable even in the presence of HCl and $Cl_2$, and that thus the radically performed side-chain chlorination can be performed without difficulty without first removing the ferric chloride. After the addition of the HMTA at the end of the first step, the dark solution is immediately lightened to a light yellow. This visible effect of the HMTA was quite apparent in the ultraviolet spectroscopic examination of ferric chloride solutions and $FeCl_3$—HMTA—$CCl_4$ solutions: not only is the absorption maximum of the ferric chloride at 275 nm shifted in the complex towards shorter wavelengths of 260 nm, but also the absorption intensity diminishes approximately by a factor of 100. These facts offer decided advantages in the initiation of radical side-chain chlorination by ultraviolet rays.

Thus, known complexing agents such as ethylenediaminetetraacetic acid, or the benzamide which is greatly stressed in Houben-Weyl 5/3, p. 736, do not have anything approaching the good action of HMTA.

The HMTA complex is poorly soluble in carbon tetrachloride, in which the chlorination is performed, but it can be washed out at the end of the reaction with methanol and water. It has also been possible to isolate the complex and subject it to elemental analysis, which showed it to have the formula $FeCl_3.2HMTA$ with 3-4 HCl.

It is advantageous to render the iron harmless because iron can result in explosive decomposition of the chlorination mixtures, as stated in Houben-Weyl 5/3, p. 736.

It is advantageous to use as the reaction vessel for these chlorination reactions tall, slender apparatus with a provision for the introduction of chlorine gas at the bottom. In the laboratory, round flasks can be used if the chlorine gas is introduced through a submerged tube about 20 mm in diameter, so that no appreciable clogging will be caused by precipitating substances.

The first step, the nuclear chlorination of xylene, is performed with ferric chlorine in e.g. carbon tetrachloride. Preferably, a 10 to 25 wt.-% solution of xylene in carbon tetrachloride is first placed in the reactor. Ferric chloride is used in amounts of 0.5 to 3.0, and preferably 1.0 to 2.5% of the weight of the xylene. On account of its more difficultly soluble secondary products, p-xylene was more greatly diluted in the chlorination than o- and m-xylene.

$AlCl_3$ and $ZnCl_2$ have proven to be poorer catalysts than $FeCl_3$.

The temperature of the first stage can be between −10° and 40° C., and preferably it is increased gradually from −10° to 40° C., preferably to +30° C. Such temperature management has proven to be best, since there is an inverse relationship between temperature and chlorine gas solubility in carbon tetrachloride on the one hand and the rate of chlorination on the other.

Chlorine is fed through a bottom nozzle or through a bottom valve into the reaction solution at a high rate of speed. At the end of the first stage, the tetrachloroxylene chlorinated in the nucleus precipitates in the form of a crystalline mass.

The second stage of the side-chain chlorination can be performed between 60° and about 85°, and generally to great advantage at temperatures of 70° to 77° C., preferably at just below the boiling point of carbon tetrachloride. Before heating, the HMTA is added in solid or dissolved form, in amounts governed according to the ferric chloride content. The weight ratio of HMTA to $FeCl_3$ is to be from 0.1 or 0.5:1 to 2.5:1, preferably from 1:1 to 2:1.

The initiation of the chlorine is performed radically, and therefore either with ultraviolet light or with compounds which decompose radically at about 70° C., such as azobisisobutyric acid nitrile, benzoyl peroxide, or other radical catalysts. It was found that, in the case of m-xylene, the initiation with azobisisobutyric acid nitrile is more effective than with ultraviolet light. The chlorination in the second stage is performed at a rate such that at first the chlorine content in the exhaust gas is less than 1% and does not increase to 20% until the end of the reaction. The reaction is always performed with a 5 to 10% excess of chlorine gas over the calculated value, for the purpose of compensating chlorine losses on the one hand, and on the other hand for avoiding any underchlorinated products that are more poorly soluble in carbon tetrachloride than the hexachloroxylenes and might contaminate the latter to a relatively great degree.

A chlorination product having a chlorine content that is 0.1 to 1.0 wt.-% higher with respect to the theoretical chlorine content of the target compound is very preferably produced in the chlorination of the side chain.

The small percentages having a $Cl_2CH$ side chain which are thus produced are easily soluble in carbon tetrachloride, in contrast to underchlorinated products.

The chlorine utilization is thus good. If it is desired to proceed more rapidly, with the lower chlorine utilization that will then result, the chlorine can be washed out of the exhaust gas with carbon tetrachloride and recycled after desorption. Carbon tetrachloride was selected as the solvent in order to forestall any exothermic reaction peaks, prevent the chlorolysis and other decompositions which occur at higher temperatures, and also permit an operation to purify the end product.

The purity of the bis-(chloromethyl)-tetrachlorobenzenes thus produced is, according to gas-chromatography analysis, between 95 and 99%, and is sufficient for a further utilization of these products.

The bis-(chloromethyl)-tetrachlorobenzenes are valuable intermediates for chemical synthesis, as for example for the preparation of the corresponding diamines, alcohols, bromides and phosphonates which are used in the fireproofing art and for other purposes. (U.S. Pat. No. 2,631,168).

EXAMPLES

Additional details on the process of preparation are set forth in the following examples.

EXAMPLES 1-6

The chlorination apparatus consists of a jacketed glass reaction tube 90 cm high, with an inside diameter of 8 cm, provided with a glass nozzle of 1.5 to 2.0 mm on its bottom, a reflux condenser on its top, and a long-shafted stirrer.

4000 g of carbon tetrachloride, 400 g of p-xylene (3.767 moles) and 8 g of ferric chloride (2.0 wt.-% with respect to the xylene) were placed in this apparatus and the solution was chilled to about 0° C. with brine. Through the bottom nozzle, 1100 g of chlorine gas was introduced at a low superatmospheric pressure. The rate of introduction of the chlorine was initially high, and was slowed towards the end of the reaction. The internal temperature was raised in the course of the chlorination to about 35° C. This first stage of the nuclear chlorination was completed in 120 to 150 minutes. Tetrachloro-p-xylene has crystallized in the form of a slushy precipitate.

The results of the side-chain chlorination in the second stage are set forth in the following table, in which the chlorination time, yield and purity of the hexachloro-p-xylene are listed in relation to the amount of HMTA added.

At the beginning of the second stage, HMTA was added to the reaction solution in the amounts given in the table below, whereupon the solution immediately became lighter in color. The temperature was increased to about 70° C., and an externally mounted 300-Watt Phillips lamp (MLU/300 W-E) was turned on. An additional 600 g of chlorine gas was introduced.

At the end of the reaction, the vessel was purged with nitrogen gas, the reaction mixture was let out of the apparatus and cooled, and the precipitated hexachloro-p-xylene was suction filtered, washed with methanol and water, and finally vacuum-dried. The purity was determined by gas chromatography (in surface-percent). 1,4-bis-chloromethyl)-tetrachlorobenzene has a melting point of 178°–179° C.

| Ex. | Amt. of HMTA (g) | Chlorination time 2nd stage (min) | Time Saved by HMTA (%) | Hexachloro-p-xylene yield (g) | (% of theory) | Purity (G.C. surface percent) |
|---|---|---|---|---|---|---|
| 1 | 0 | about 500 | 100 | 810 | 68.7 | 92.9 |
| 2 | 4 | 465 | 93 | 830 | 70.4 | 94.0 |
| 3 | 8 | 130 | 26 | 880 | 74.7 | 96.4 |
| 4 | 10 | 105 | 21 | 890 | 75.5 | 96.5 |
| 5 | 12 | 75 | 15 | 1024 | 86.9 | 95.7 |
| 6 | 16 | 225 | 45 | 900 | 76.4 | 96.0 |

As it can be seen, HMTA makes possible a great reduction of the chlorination time and also brings about increased yields and improves the purity of the target substance.

EXAMPLES 7 AND 8

In the same chlorination apparatus, and at the same temperature conditions as described in Examples 1–6, 400 g of p-xylene was chlorinated in the nucleus with 1100 g of Cl$_2$, in 4000 g of carbon tetrachloride as before, but in the presence of 7.56 g of ferric chloride (1.89% with respect to the xylene). After this 1st step, HMTA was added (amounts in the following table), the mixture was heated at about 70° C., 4 g of azo-bis-isobutyric acid nitrile was added, and an additional 600 g of chlorine gas was introduced. After the chlorination had ended, approximately 1.2 liters of carbon tetrachloride were distilled out, the reaction mixture was cooled to about 10° C., and was worked up as in Examples 1 to 6.

| Example | Amt. of HMTA (g) | Chlorination time of 2nd stage (min) | Hexachloro-p-xylene yield (g) | (% of the theory) |
|---|---|---|---|---|
| 7 | 7.56 | 180 | 1040 | 88.3 |
| 8 | 9.0 | 130 | 1085 | 92.1 |

EXAMPLES 9–12

In a four-necked flask provided with thermometer, stirrer, condenser and a 20 mm diameter chlorine introduction tube, 212 g of m-xylene (1.997 moles) in 1.2 liters of carbon tetrachloride was placed, and was chlorinated in the nucleus in 5 to 6 hours in the presence of 4 g of ferric chloride with 600 g of chlorine gas (6% excess) at temperatures increasing gradually from 0° to 20° C. The chlorination was performed at such a rate that, in the beginning no chlorine was detected in the exhaust gas, and during the injection of the final 50 g of chlorine approximately 10% of chlorine was detected in the exhaust gas.

For the side-chain chlorination, the reaction mixture was heated to about 70° C. and an additional 300 g of chlorine was slowly and steadily added. The chlorination times determined are given in the following table for initiation with ultraviolet light and with azo-bis-isobutyric acid nitrile (AIBN), with and without the addition of HMTA.

The resultant mixtures were not worked up.

| Example | HMTA Added (4g) | Ultra-violet rad. | AIBN Added (2.12 g) | Chlorination time in 2nd stage (h) | Chlorine in exhaust (%) |
|---|---|---|---|---|---|
| 9 | – | + | – | 24 | 10–50 |
| 10 | + | + | – | 3.5 | 0–20 |
| 11 | – | – | + | 23.5 | 10–50 |
| 12 | + | – | + | 2.5 | 0–10 |

HMTA thus brings about a substantially faster absorption and reaction of the chlorine combined with even lower chlorine contents in the exhaust.

EXAMPLE 13

In a 250 liter enameled autoclave flushed out with nitrogen, equipped with an impeller stirrer and a water-cooled ultraviolet immersion lamp (Hanau brand, 2 kW), and also with a condenser, 40 kg of m-xylene, 300 kg of carbon tetrachloride and 0.5 kg of ferric chloride (1.25 wt.-% with respect to the xylene) were combined. 115 kg of chlorine gass was injected through the bottom valve at temperatures gradually increasing from 10° to 40° C., at a rate of about 5 kg of chlorine gas per hour.

After 24 hours, 0.5 kg of hexamethylenetetramine was added, the ultraviolet lamp was turned on, and another 60 kg of chlorine gas was injected at a slightly slower rate over a period of about 16 hours at about 60° C. After the chlorination had ended, chlorine and hydrogen chloride residues were blown out with air, about 100 kg of carbon tetrachloride was distilled out, and the solution was cooled to about 10° C. The no more than partially precipitating product was isolated, washed once with carbon tetrachloride and twice with methanol, and vacuum dried.

Yield: 72.5 kg (61.6% of the theory).
Melting point: 139°–141° C.
Gas chromatographic purity: 97.0%.

EXAMPLE 13 A (comparison)

The same procedure could not be performed in the second stage without the addition of hexamethylenetetramine. This side-chain chlorination was possible at a satisfactory speed only after the 1st stage had been isolated and the ferric chloride had been removed.

EXAMPLE 14

In a 250-liter enameled autoclave equipped with an impeller stirrer and condenser, 40 kg of m-xylene, 300 kg of carbon tetrachloride and 0.5 kg of ferric chloride (1.25 wt.-% with respect to the m-xylene) were combined. Through the bottom valve, 115 kg of chlorine gas was injected at a rate of about 5 kg per hour at temperatures increasing gradually from 10 to 40 degrees C.

Then 0.6 kg of hexamethylenetetramine and 0.5 kg of Profor N ® (a preparation of AIBN) were added and another 60 kg of chlorine was injected at a rate of about 4 kg per hour through the bottom valve at about 60 degrees C. After the chlorination had ended, residues of chlorine and hydrogen chloride were flushed out with air, about 100 kg of carbon tetrachloride were distilled out, and the mixture was cooled. The solid substance was isolated, washed once with carbon tetrachloride and twice with methanol and vacuum dried.

Yield: 85.5 kg (72.0% of the theory).
M.P.: 139°–141.5° C.
Gas chromatographic purity: 98.2%.

The carbon tetrachloride mother liquors could be used for a subsequent batch, resulting in better yields of about 90% of the theory.

What is claimed is:

1. In the process of preparing bis-chloromethyl tetrachlorobenzene of the formula

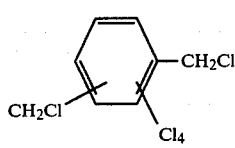

(I)

which comprises in a first stage contacting xylene with chlorine for formation of tetrachloroxylene, in the presence of FeCl$_3$ or FeCl$_3$.6H$_2$O as catalyst for the reaction, and in a second stage contacting the tetrachloroxylene with chlorine for formation of said tetrachlorobenzene in the presence of ultraviolet light or a compound which decomposes radially a radical catalyst for the second stage reaction, the improvement which comprises performing the second stage at a temperature of 60°–85° C. in the presence of the catalyst from the first stage and in the presence of hexamethylenetetramine for complexing with the catalyst, the weight ratio of hexamethylenetetramine to ferric chloride present in the second stage being from 0.1:1 to 2.5:1.

2. The process of claim 1, wherein an organic solvent is employed as the reaction medium.

3. Process of claim 2, wherein the organic solvent is carbon tetrachloride.

4. Process of claim 1, wherein the weight ratio of hexamethylenetetramine to ferric chloride present in the second stage is 1:1 to 2:1.

5. Process of claim 1, wherein the temperature for the first stage is −10° to +40° C.

6. Process of claim 1, wherein the xylene is overchlorinated and the chlorine content of the product of the second stage is 0.1 to 1.0 weight % higher than the theoretical chlorine content of said bis-chloromethyl tetrachlorobenzene.

7. Process of claim 1, wherein said tetrachlorobenzene is o-bis-chloromethyl tetrachlorobenzene and the xylene is o-xylene.

8. Process of claim 1, wherein said tetrachlorobenzene is m-bis-chloromethyl tetrachlorobenzene and the xylene is m-xylene.

9. Process of claim 1, wherein said tetrachlorobenzene is p-bis-chloromethyl tetrachlorobenzene and the xylene is p-xylene.

10. Process of claim 1, wherein the first and second stages are performed in a single reaction vessel.

11. Process of claim 1, wherein the bis-chloromethyl-tetrachlorobenzene is precipitated from the reaction medium and the precipitated product has a purity of 95–99%.

12. Process of claim 1, wherein the weight proportion of hexamethylenetetramine to the FeCl$_3$ of the catalyst is 0.5:1 to 2.5:1.

13. Process of claim 1, wherein the amount of catalyst is 0.5 to 5% by weight with respect to the xylene.

* * * * *